US008327797B1

(12) United States Patent
Morales-Ramos et al.

(10) Patent No.: US 8,327,797 B1
(45) Date of Patent: Dec. 11, 2012

(54) SYSTEM AND METHOD FOR PRODUCTION OF PREDATORY MITES

(75) Inventors: Juan Morales-Ramos, Greenville, MS (US); Maria Rojas, Greenville, MS (US); Daniel Cahn, Camarillo, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 501 days.

(21) Appl. No.: 12/432,313

(22) Filed: Apr. 29, 2009

(51) Int. Cl.
*A01K 29/00* (2006.01)
(52) U.S. Cl. ......................................................... 119/6.5
(58) Field of Classification Search .................... 119/6.5, 119/416, 270; 449/2, 3, 9, 10, 48
See application file for complete search history.

(56) References Cited

U.S. PATENT DOCUMENTS

| | | | |
|---|---|---|---|
| 4,850,305 A * | 7/1989 | Georgi et al. .................. | 119/6.6 |
| 4,966,329 A | 10/1990 | Show | |
| 5,351,643 A * | 10/1994 | Hughes .......................... | 119/6.5 |
| 5,398,642 A * | 3/1995 | Harwich ......................... | 119/6.5 |
| 6,105,535 A * | 8/2000 | Atamian et al. ................ | 119/6.5 |
| 6,244,213 B1 * | 6/2001 | Tedders et al. ................. | 119/6.6 |
| 6,291,007 B1 | 9/2001 | White et al. | |
| 6,397,782 B1 * | 6/2002 | Cope et al. ..................... | 119/452 |
| 7,051,672 B2 | 5/2006 | Wright | |
| 7,174,847 B1 * | 2/2007 | Hulteen, III ................... | 119/6.5 |

* cited by examiner

*Primary Examiner* — Kristen C Hayes
(74) *Attorney, Agent, or Firm* — John Fado; Robert D. Jones; Lesley Shaw

(57) ABSTRACT

Predatory mites contained in an enclosed housing are provided with a continuous food source (i.e. spidermites) so that the healthy adult predatory mites migrate upwards to a collection container at the apex of the housing where a user harvests the predatory mites. The predatory mites are provided with spidermite-infested vegetation disposed in planar trays. The trays are chronologically arranged in a vertical stack within the housing so that as new trays loaded with spidermites are added to the top of the stack, old trays depleted of spidermites are removed from the bottom of the stack. The predatory mites intuitively display negative geotropism and positive phototropism so that the mites naturally move upwards and toward the light. Consequently the predatory mites migrate to the upper trays as new trays are added and eventually reach the collection container at the apex of the housing.

17 Claims, 5 Drawing Sheets

SYSTEM AND METHOD FOR PRODUCTION OF PREDATORY MITES

FIELD OF THE INVENTION

The present invention relates to a system and method of continuously producing predatory mites. Specifically, the invention relates to a system and method of providing predatory mites a continuous supply of food so that successive generations of mites hatch, feed, and move into a collection container.

BACKGROUND OF THE INVENTION

Spidermites (*Tetranychus urticae*) are one of the most common insect pests. Spidermites are the direct cause of millions of dollars in damage per year to a wide variety of plant types. Spidermites generally attach themselves to the leaves of a plant and suck the moisture out of plant foliage. Spidermites will stunt or wilt new plant growth and, in severe infestations, may kill the host plant. Spidermites are particularly damaging to plants that are already subject to heat or drought-related stress.

Predatory mites feed on spidermite eggs and adult spidermites, and are one means of controlling spidermite populations. Predatory mites are particularly popular with organic growers seeking non-chemical biological pest control agents. The predatory mites are generally quicker and more agile (although not necessarily larger) than the spidermites that they prey on, and they can seek out prey in areas that may be missed or are inaccessible to perfunctory chemical sprays. Additionally, unlike chemical sprays, spidermites cannot develop a tolerance or immunity to predatory mites. Predatory mites may also be used against several species of thrips.

Predatory mites are a particularly successful pest control agent in greenhouses because of the high degree of control that the grower has over the greenhouse environment. The most prolific and effective types of predatory mites function best in a specific temperature and humidity envelope. However, several predatory mite species are successfully used to suppress spidermites in non-greenhouse environments on crops such as apples, citrus, and avocados as well as strawberries and raspberries.

In the preferred embodiment, the current invention is directed to producing the predatory mite *Phytoseiulus persimili*. However, the invention may also be used to produce a variety of other mites and insects. For the purposes of this patent specification, the term "predatory mites" will be used to generally refer to any mite species that feeds on other arthropods.

Predatory mites are currently produced and marketed by several commercial organizations. An index of beneficial insect producers (including predatory mite producers) is available from www.bugladyconsulting.com/Suppliers%21of%21beneficial%21insects.htm.

Most predatory mite production is currently done in greenhouses in an essentially uncontrolled manner. Predatory mites are simply deposited on vegetation that is infested with spidermites and left for a pre-determined amount of time. Workers then harvest the predatory mites remaining in the vegetation. Strict protocols (and generally separate greenhouses) are required to keep the predatory mites separate from the spidermites until a specifically prescribed stage in the production process. The prior art process is not continuous and one cycle requires about six weeks from start to harvest.

While the prior art method is simple, it is also relatively labor-intensive and inefficient, and it results in inconsistent harvests. Further, there is always a significant time gap between the start of the predatory mite production process and the window in which the mites can be harvested.

The need exist for a systematic means of continuously feeding and harvesting predatory mites so that good quality predatory mites are produced. The current invention provides an enclosed, modular, and systematic means of continuously producing healthy predatory mites. Once the system is up and running, maintaining the system requires minimal operator skill and knowledge and enables the operator to produce predatory mites for an essentially indefinite period of time. In laboratory tests, the process of the current invention has been shown to increase predatory mite production by 21-300% relative to prior art processes involving similar time periods and similar resources.

SUMMARY OF THE INVENTION

The disclosure is directed to a system for producing arthropods (predatory mites). The system includes an enclosed housing (a "cage") with an upper portion and a lower portion. A plurality of predatory mites and a food source (spidermites) are introduced into the lower portion of the cage. A collection container is attached to the upper portion of the cage. In operation, the predatory mites consume the spidermites and the offspring of the predatory mites migrate upward into the collection container for harvest.

The invention is also directed to a method of producing predatory mites. An operator provides an enclosed cage with an upper portion and a lower portion. A collection container is positioned adjacent the upper portion. A plurality of predatory mites and spidermites are introduced into the lower portion. An operator then periodically harvests the offspring of the predatory mites from the collection container adjacent to the upper portion of the cage.

DETAILED DESCRIPTION OF PREFERRED EMBODIMENTS

Figure 1:
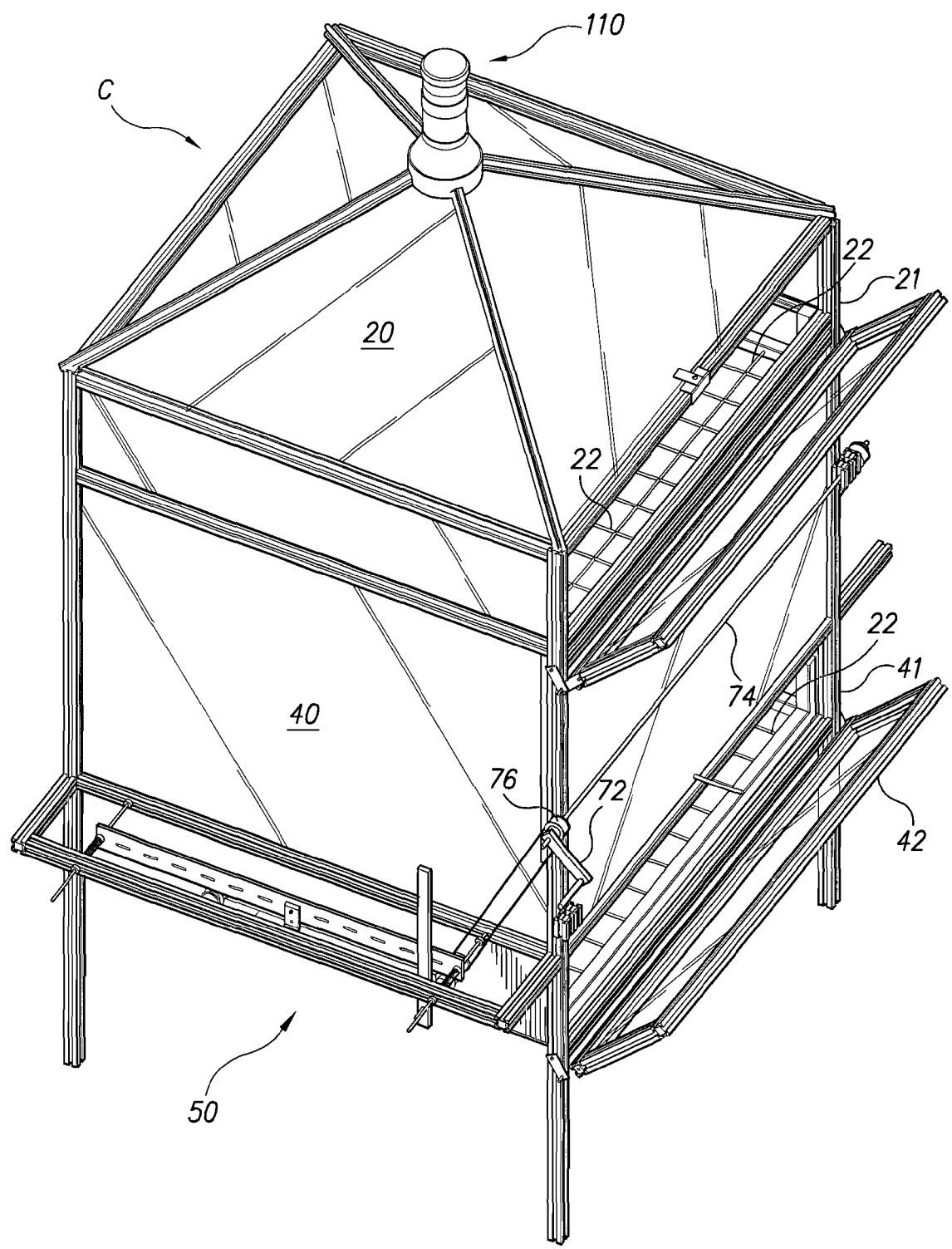
FIG. 1 is a perspective view of the cage.

The present invention comprises a system and method for continuously producing predatory mites. As generally shown in FIG. 1, the system comprises a translucent enclosed housing C with an upper portion 20 and a lower portion 40. The lower portion 40 includes an upper access means 21, a lower access means 41 and a tray transfer assembly 50. A collection apparatus 110 is connected to the upper portion 20 of the housing C.

Figure 2:
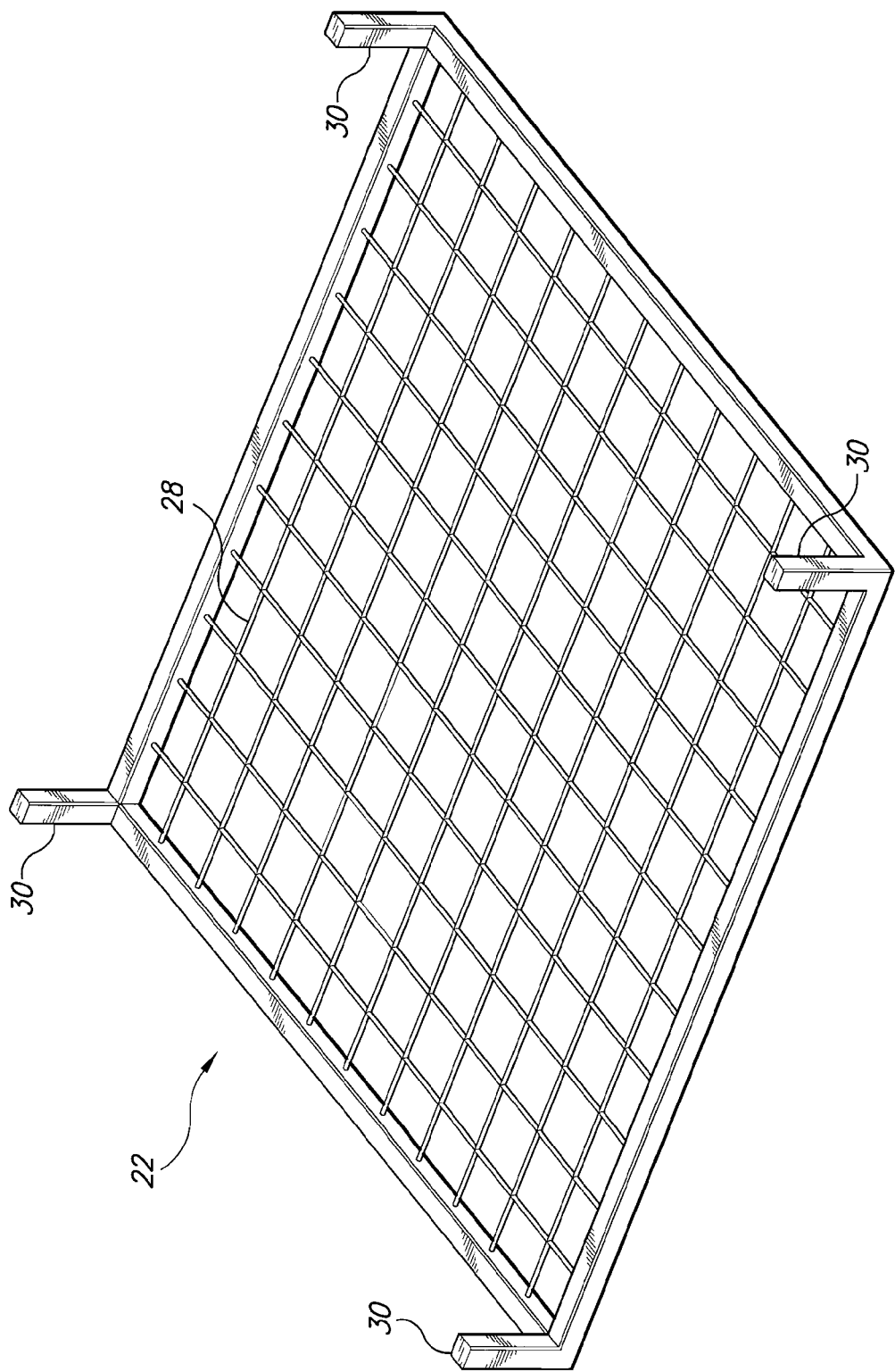
FIG. 2 is a perspective view of an empty tray.
Figure 3:
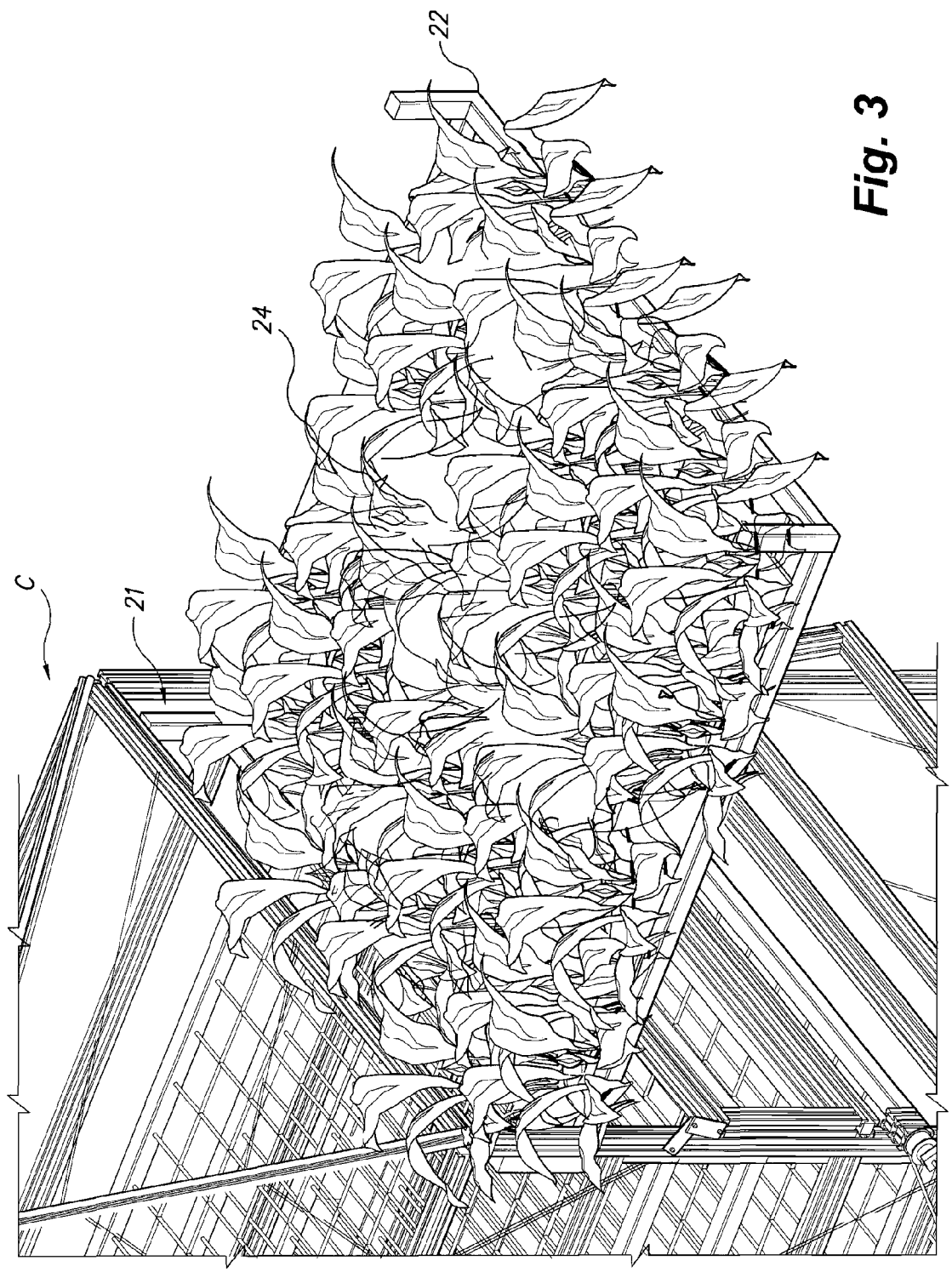
FIG. 3 is a perspective view of the cage at the beginning of the predatory mite production process as the first tray of infested vegetation is added to the cage. The sides of the cage are shown as transparent so that the tray stack within the cage is visible.

In the preferred embodiment, the enclosed housing comprises a "cage" C, and the upper and lower access means comprise upper 21 and lower 41 "windows". The cage C holds multiple stackable trays 22 of the type best shown in FIG. 2. As shown in FIG. 3, at the beginning of the predatory mite production process, vegetation infested with spidermites is deposited on the first tray 22 and placed in the cage C through the upper window 21. FIG. 3 shows the sides of the cage C as transparent so that the tray stack within the cage C is visible. Predatory mites are deposited on the vegetation 24 so that the predatory mites eventually consume the spidermites that infest the vegetation 24. As the process progresses, new trays 22 loaded with infested vegetation 24 are added to the upper window 21, and old trays 22 depleted of spidermites with dead vegetation are removed through the lower window 41. The tray transfer mechanism 50 (best shown in FIG. 4) is used to lower the stack of trays 22 each time a new tray 22 is added to the top of the stack through the upper window 21. As the trays 22 in the upper portion of the cage C become saturated with predatory mites, the predatory mites naturally migrate further upward into the collection apparatus 110. The preferred embodiment of the collection apparatus is shown in detail in FIG. 5.

The current invention takes advantage of the predatory mites' natural instincts to move up (negative geotropism) and towards a light (positive phototropism). This instinct ensures that as new predatory mites hatch and mature, the healthy predatory mites move upwardly into the new incoming trays, and then further upwardly to the collection apparatus 110 where they are harvested. Living organisms (including insects and mites) that naturally move or grow upwardly (most likely using gravity as an orienting stimulus) display negative geotropism. Similarly, organisms (including insects and mites) that naturally move or grow in the direction of light display positive phototropism. Although the preferred embodiment is directed specifically to predatory mites, other arthropods (including insects) that display negative geotropism and/or positive phototropism should be considered within the scope of the disclosure.

The invention is discussed in greater detail infra.

As generally shown in FIG. 1 and briefly discussed supra, the system of the current invention has a generally modular design so that the predatory mite breeding and feeding processes occur within the cage C. In the preferred embodiment, the cage C is translucent and generally semi-transparent so that at least some light penetrates the walls of the cage C. In alternative embodiments, the cage C may be completely transparent, or the lower portion 40 may be opaque and the upper portion 20 may be more translucent so that the predatory mites are drawn toward the upper portion 20 of the cage C. In the preferred embodiment, at least the collection container 114 (see FIG. 5) is generally transparent.

A drape such as a plastic tarp or a shower curtain may be disposed around the cage to aid in the control of the relative humidity within the cage. The predatory mites of the preferred embodiment (*Phytoseiulus persimili*) reproduce and function most effectively when the relative humidity is approximately 70% and the temperature is between 59° F. and 86° F.

At the initiation of the predatory mite production process, vegetation 24 is collected on a series of trays 22. As best shown in FIG. 2, in the preferred embodiment, each tray 22 is comprised of a rectangular frame 26 with a polypropylene net 28 extending over the interior of the frame 26. A leg 30 projects upwardly from each corner of the tray 22 so that the trays 22 can be easily stacked.

In the preferred embodiment, vegetation 24 is collected on the trays 22 through a specific growing process. A plant container (not shown) is planted with vegetation 24 and a tray 22 is placed immediately above the plant container. The vegetation 24 grows upwardly through the frame net 28 and then spreads outward as the leaves further develop and grow. When the vegetation 24 is fully grown and the tray 22 is ready to be used, the vegetation 24 is infested with spidermites and clipped off at ground level by an electric hedge trimmer (or the like) so that the vegetation 24 above the net 28 is supported by the tray 22 (See FIG. 3).

In the preferred embodiment, the vegetation 24 is comprised of multiple bean plants. In alternative embodiments, the vegetation 24 may be of any variety known in the art so long as the vegetation 24 is able to support the growth of the spidermites. Similarly, the vegetation 24 may be grown, gathered, and deposited on the trays in any manner known in the art.

As shown in FIG. 3, once the vegetation 24 has been gathered and infested with spidermites, a first tray 22 loaded with infested vegetation 24 is inserted in the upper window 21 of the cage C. In FIG. 3, the sides of the cage C are shown as transparent so that the tray 22 stack is partially visible. Approximately 2 to 3 days after the first tray 22 is placed in the cage C, a new tray 22 with infested vegetation 24 is added to the upper window 21 and a tray 22 is removed from the lower window 41. This tray 22 addition/removal cycle is repeated in another 2 to 3 days and may continue indefinitely thereafter. Predatory mites that are ready for harvest generally begin to appear in the collection apparatus 110 about 3 days after the initiation of the process.

In the preferred embodiment, there are four trays in the cage C during the predatory mite production process. Although the first few trays 22 removed from the lower window 41 will be completely empty, beginning with the fourth tray 22, the removed trays will be filled with dead vegetation 24 and will be generally depleted of spidermites. Essentially, it takes three tray addition/removal cycles for an exemplary tray 22 to move from the top position in the tray stack to the bottom position in the tray stack. During the fourth tray 22 addition/removal cycle, the exemplary tray 22 is removed from the cage C.

As best shown in FIG. 1, in the preferred embodiment, the upper 21 and lower 41 windows are essentially identical in design. The upper and lower windows 21, 41 are generally comprised of hinged rectangular panels 32, 42. The windows 21, 41 must be of sufficient size to easily accommodate a user maneuvering successive trays 22 into and out of the windows 21, 41.

In alternative embodiments, the windows 21, 41 and trays 22 may be of any shape or design known in the art consistent with their associated function. Although the windows 21, 41 are shown as having a rectangular shape, they may have other shapes, as required, to enable an operator to maneuver trays 22 into and out of the cage C. The number of trays 22 in the cage C during the production process may be more or less than the four trays 22 of the preferred embodiment. Further, the time intervals associated with the tray 22 addition/removal cycle may vary depending upon multiple factors associated with the process. Additionally, more than one tray 22 may be added or removed in a given cycle.

In additional alternative embodiments, the entire upper and/or lower and/or front and/or back and/or side portions of the cage C may be hinged or removable so that a user can directly add or remove trays 22 in the cage C without the need for windows 21, 41 or the tray transfer assembly 50. The trays 22 may also be positioned in a rack within the cage C so that the trays 22 are not stackable and the rack directly supports the weight of the trays 22.

With regard to the tray transfer assembly 50, there are multiple means known in the art for manipulating the tray stack described herein. The trays 22 may be lowered or otherwise shifted with a hand cranked mechanism (as described in the preferred embodiment) or through a powered means such as an electrical, hydraulic, or pneumatic motor (or the like). The movement of the trays 22 may be automated based on a timer or based on operator-supplied programmable instructions, or any other means known in the art.

Figure 4:
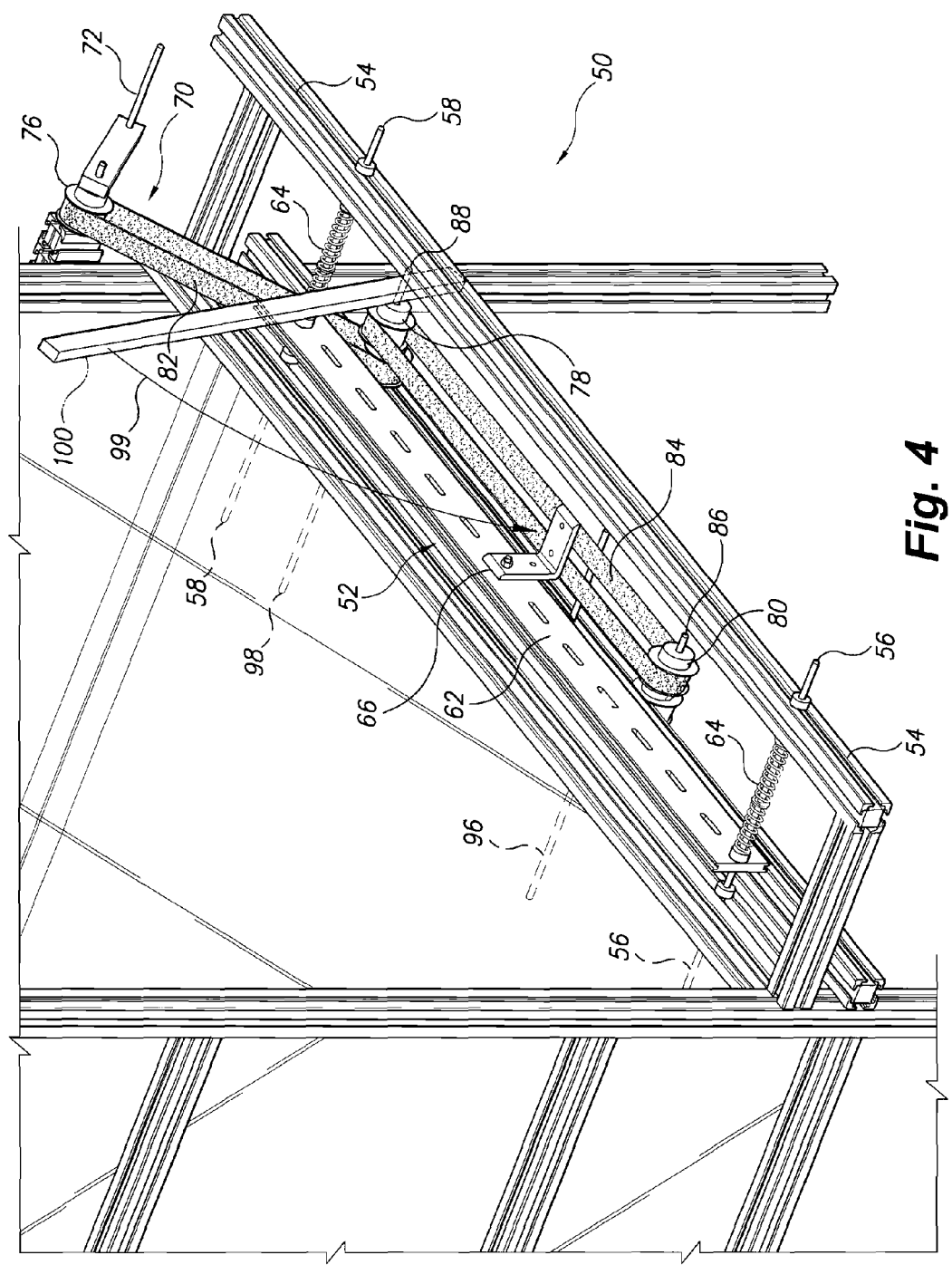
FIG. 4 is a perspective view of the tray transfer assembly in the raised position (pins extended).

The tray transfer assembly 50 of the preferred embodiment is generally shown in FIG. 4. The tray transfer assembly 50 comprises a support pin control apparatus 52, and a tray lowering mechanism 70 disposed on each side of the cage C. Specifically, a first support pin control apparatus 52 and a first tray lowering mechanism 70 are disposed on one side of the cage C, and a second support pin control apparatus and a second tray lowering mechanism are disposed on a second (opposite) side of the cage C. Essentially, the support pin control apparatus 52 and tray lowering mechanism 70 on the first side of the cage C is a mirror image of the support pin control apparatus and tray lowering mechanism on the second side of the cage C (with the exception of hand crank 72). As shown in FIG. 1, a common shaft 74 extends across the front of the cage C and connects the tray lowering mechanisms 70 on each side of the cage C. For the sake of simplicity, only one support pin control apparatus 52 and one tray lowering mechanism 70 will be described and shown in detail (see FIG. 4), however it should be understood that the components described are duplicated on both sides of the cage C.

With regard to the support pin control apparatus 52, as shown in FIG. 4, the support pin control apparatus 52 is comprised of a support frame 54 extending outwardly away from the cage C. Elongated support pins 56, 58 extend through the support frame 54 and into the cage C. The support pins 56, 58 also extend through a retraction bar 62 positioned between the support frame 54 and the cage C. Compression springs 64 are disposed around the support pins 56, 58 between the retraction bar 62 and the support frame 54 so that the compression springs 64 urge the retraction bar 62 towards the cage C and away from the support frame 54. An "L" shaped locking bracket 66 is also attached to the retraction bar 62.

FIG. 4 shows the retraction bar 62 in the released position so that the support pins 56, 58 are extended into the cage C. FIG. 4 shows the cage C as empty, however during the normal production process, the bottom tray 22 is supported by the support pins 56, 58 and swing pins 96, 98 shown in FIG. 4.

Figure 5:
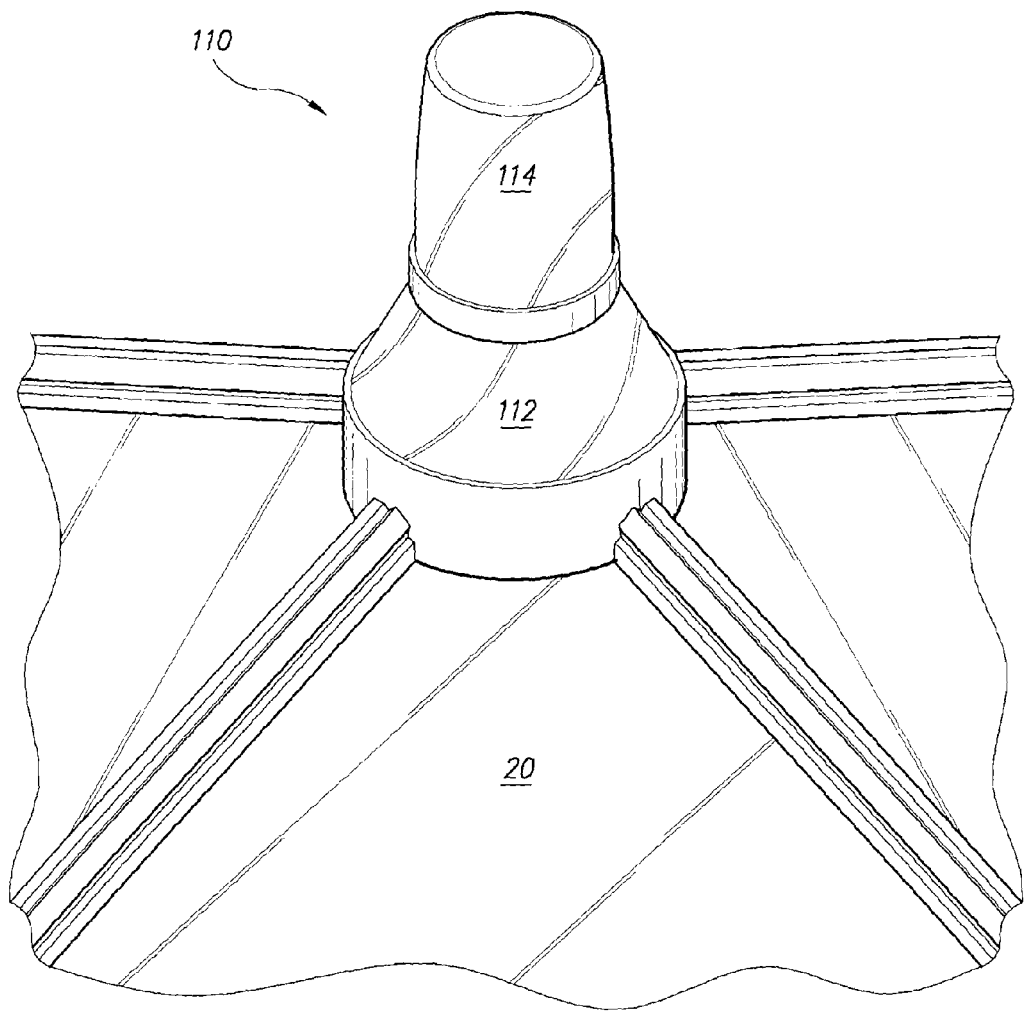
FIG. 5 is a perspective view of the mite collection apparatus.

With regard to the tray lowering mechanism 70, as shown in FIG. 5, the tray lowering mechanism 70 is comprised of an upper pulley 76 in communication with first 78 and second 80 lower pulley assemblies. A fan belt-type elastomeric band 82 connects the upper pulley 76 with first lower pulley assembly 78, and a similar second band 84 connects the first lower pulley assembly 78 with the second lower pulley assembly 80.

As discussed supra, a common shaft 74 (see FIG. 1) extends across the front of the cage C and connects the upper pulleys 76 on each side of the cage C. In the preferred embodiment, a hand crank 72 is disposed on the upper pulley 76 on one side of the cage C. Turning the hand crank 72 causes the upper pulleys 76 and lower pulley assemblies 78, 80 on each side of the cage C to rotate simultaneously.

As best shown in FIG. 4, the lower pulley assemblies 78, 80 further comprise shafts 86, 88 that extends through structural bracing and into the cage C. The shafts 86, 88 are connected to generally "L" shaped swing arms. Only the horizontally extending end portions 96, 98 of the swing arms are visible in FIG. 4. As also shown in FIG. 4, a vertically extending trip bar 100 is disposed on the shaft 88 along with the first lower pulley assembly 78 so that rotating the hand crank 72 also rotates the trip bar 100.

In operation, the tray lowering mechanism 70 (in coordination with the pin control apparatus 52) lowers the bottom tray 22 so that the tray 22 is accessible through the lower window 41. As best shown in FIG. 5, in normal production mode, the support pins 56 and 58 extend into the cage C and the swing arms are in the raised position so that both the support pins 56, 58 and the swing pins 96, 98 (associated with the swing arms) support the bottom tray 22. After a new tray 22 is added to the upper window 21, a tray 22 must be removed from the lower window 41. To remove a tray from the lower window 41, the bottom tray must be lowered and the pins 56, 58, 96, 98 supporting the bottom tray 22 must be transitioned to support the next lowest tray 22 thereby freeing the bottom tray 22 for removal.

To accomplish the transition, a user first retracts the pins 56, 58 from the interior of the cage C by pulling the retraction bar 62 away from the cage C. The locking bracket 66 is then connected to the support frame 54 so that the retraction bar 62 is retained in a distal position relative to the cage C. After the support pins 56, 58 are retracted, only the swing pins 96, 98 remain to support the bottom tray 22 in the stack.

To move the bottom tray 22 downwardly, a user turns the hand crank 72 so that the swing arms and associated swing pins 96, 98 start to move downwardly. Simultaneously the trip bar 100 rotates in the direction of the arrow 99. As the hand crank 72 is rotated, the trip bar 100 contacts the locking bracket 66 on the retraction bar 62 and thereby causes the locking bracket 66 to detach from the support frame 54. As the locking bracket 66 detaches, the compression springs 64 propel the retraction bar 62 and associated support pins 56, 58 inward toward the cage C so that the support pins 56, 58 catch and support the next tray 22 above the bottom tray 22. Since the tray 22 stack now rests on the next tray above the bottom tray, the support pins 56, 58 effectively support the tray stack. A user can then freely slide the bottom tray 22 out of the cage C without affecting the other trays 22 in the stack. Once the lowest tray 22 has been removed, the user simply rotates the hand crank 72 until the swing pins 96, 98 are once again in position under the (new) bottom tray 22.

As described supra, at periodic intervals during the process predatory mites are collected in the collection apparatus 110 connected to the upper portion 20 of the cage C. In the preferred embodiment, predatory mites are harvested 2-3 days after initiation of the process and every 2-3 days thereafter. As shown in FIG. 5, the collection apparatus 110 comprises a funnel component 112 positioned adjacent to the upper portion 20 of the cage C, and a collection container 114 connected to the funnel component 112. In the preferred embodiments, the collection container 114 is generally transparent and screws onto the funnel component 112. An operator can simply observe the collection container 114 to detect the presence and concentration of predatory mites in the container 114.

In alternative embodiments, the harvest frequency may be varied based on the volume of the food source supplied and the population density of the predatory mites within the cage C. The exact structure of the collection apparatus 110 may also be varied so that the funnel component 112 is elongated, truncated, or segmented. The size and shape of the collection container 114 may also be varied. In further alternative embodiments, a light source may be positioned in or adjacent to the components of the collection apparatus 110 to provide added stimulus to draw the predatory mites to the collection apparatus 110.

For the foregoing reasons, it is clear that the invention provides an innovative system and method for continuously producing predatory mites. The invention may be modified in multiple ways and applied in various technological applications. The current invention may be modified and customized as required by a specific operation or application, and the individual components may be modified and defined, as required, to achieve the desired result. Although the materials of construction are not described, they may include a variety of compositions consistent with the function of the invention. Such variations are not to be regarded as a departure from the spirit and scope of the invention, and all such modifications as would be obvious to one skilled in the art are intended to be included within the scope of the following claims.

What is claimed is:

1. A system for producing arthropods comprising:
an enclosed housing, the housing comprising an upper portion and a lower portion, and an upper access means and a lower access means; the housing being structured so that a plurality of arthropods are deposited in the lower portion;
a food source for the arthropods, the food source being deposited in the lower portion;
a vertical column of trays within the housing, the food source being disposed on the trays; legs of upper filled trays resting on legs of lower filled trays;
a tray transfer assembly; and,
a collection container, the collection container being attached to the upper portion;
whereby the housing is structured so that the food source is deposited onto a tray and into the housing through the upper access means, and remains of the food source is removed through the lower access means.

2. The system of claim 1 wherein the arthropods display negative geotropism.

3. The system of claim 1 wherein the arthropods display positive phototropism.

4. The system of claim 1 wherein the arthropods comprise predatory mites.

5. The system of claim 4 wherein the predatory mites comprise *Phytoseiulus persimili*.

6. The system of claim 1 wherein the food source comprises prey arthropods.

7. The system of claim 6 wherein the prey arthropods comprise spidermites.

8. The system of claim 7 wherein the spidermites comprise *Tetranychus urticae*.

9. The system of claim 1 wherein the tray transfer assembly comprises a tray lowering mechanism and a support pin control apparatus disposed on each side of the cage so that the support pin control apparatus on a first side of the cage is a mirror image of the support pin control apparatus on a second side of the cage.

10. The system of claim 1 wherein the upper portion comprises a funneling mechanism for funneling the arthropods to the collection container.

11. The system of claim 1 wherein the collection container is positioned at an apex of the upper portion.

12. A method of producing arthropods, the method comprising the steps of:
(a) providing an enclosed housing having an upper access means and a lower access means;
(b) positioning a collection container adjacent an upper portion of the housing;
(c) introducing a plurality of arthropods into a lower portion of the housing;
(d) supplying the arthropods with a food source through the upper access means and removing remains of the food source through the lower access means;
(e) harvesting offspring of the arthropods from the collection container.

13. The method of claim 12 wherein the arthropods display one of negative geotropism or positive phototropism.

14. The method of claim 12 wherein the arthropods comprise predatory mites.

15. The method of claim 14 wherein the food source comprises spidermites.

16. The method of claim 12 wherein, in step (e), the collection container is positioned at an apex of the upper portion.

17. A system for producing arthropods comprising:
an enclosed housing, the housing having an upper access means and a lower access means, and a vertical column of trays extending between the upper access means and the lower access means, legs of upper filled trays resting on legs of lower filled trays, the system further comprising a tray transfer assembly;
the housing being structured so that a plurality of arthropods and a food source are deposited in the upper access means, and remains of the food source is removed through the lower access means;
a collection container, the collection container being attached to an apex of the housing so that the collection container is positioned above the housing.

* * * * *